United States Patent
Anelli et al.

[11] Patent Number: 6,099,824
[45] Date of Patent: *Aug. 8, 2000

[54] BENZYLOXY DERIVATIVES OF DTPA FOR MRI

[75] Inventors: Pier Lucio Anelli; Andrea Beltrami; Fulvio Uggeri; Mario Virtuani, all of Milan, Italy

[73] Assignee: Dibra S.p.A., Milan, Italy

[ * ] Notice: This patent issued on a continued prosecution application filed under 37 CFR 1.53(d), and is subject to the twenty year patent term provisions of 35 U.S.C. 154(a)(2).

[21] Appl. No.: 08/904,646

[22] Filed: Aug. 1, 1997

[30] Foreign Application Priority Data

Aug. 2, 1996 [IT] Italy .................. MI96A1687

[51] Int. Cl.[7] .................. A61B 5/055
[52] U.S. Cl. .................. 424/9.364; 534/16; 556/50; 556/55; 556/63; 556/77; 556/105; 556/116; 556/134; 556/148; 514/492; 514/502; 514/836; 562/405; 562/500; 562/507
[58] Field of Search .................. 424/9.364; 534/16; 556/50, 55, 63, 77, 105, 116, 134, 148; 514/492, 502, 836; 600/420; 436/173; 562/500, 507, 405

[56] References Cited

U.S. PATENT DOCUMENTS

| | | | |
|---|---|---|---|
| 4,505,956 | 3/1985 | Yamamoto et al. | 427/393.1 |
| 5,057,302 | 10/1991 | Johnson et al. | 424/1.1 |
| 5,182,370 | 1/1993 | Felder et al. | 534/16 |
| 5,453,264 | 9/1995 | Mori et al. | 424/9.364 |
| 5,547,817 | 8/1996 | Okada et al. | 430/393 |
| 5,567,411 | 10/1996 | Keana et al. | 424/9.1 |
| 5,582,814 | 12/1996 | Scott et al. | 424/9.364 |
| 5,672,335 | 9/1997 | Krause et al. | 424/9.42 |
| 5,695,737 | 12/1997 | Krause et al. | 424/1.65 |
| 5,733,522 | 3/1998 | Schimtt-Willich et al. | 424/1.65 |
| 5,746,995 | 5/1998 | Maier et al. | 424/1.65 |
| 5,885,548 | 3/1999 | Maier et al. | 424/1.65 |

FOREIGN PATENT DOCUMENTS

WO 82/03880 11/1982 WIPO .
96/16677 11/1995 WIPO .

OTHER PUBLICATIONS

Lauffer et al., Radiology 207(2):529–538 (1998).
Kroft et al., Journal of Magnetic Resonance Imaging 10:395–403 (1999).

Primary Examiner—Gary E. Hollinden
Attorney, Agent, or Firm—Nixon & Vanderhye P.C.

[57] ABSTRACT

Compounds which can chelate paramagnetic bi- and trivalent metal ions, their chelates with said metal ions and their use as contrast agents in magnetic resonance imaging (MRI), the compounds having formula (I)

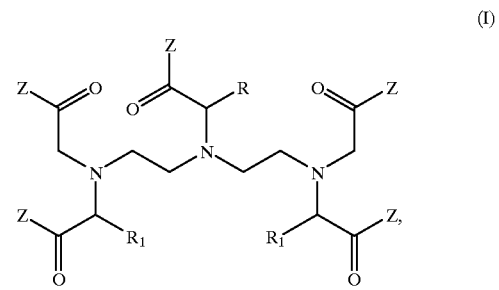

(I)

wherein

R is a —$(CH_2)_m$—O—$R_2$ group or hydrogen, $R_2$ is a ($C_6$–$C_{10}$) aryl, or an alkyl($C_1$–$C_5$)-aryl($C_6$–$C_{10}$) group, substituted or not by a group L corresponding to a OH group or a $OR_3$ group, wherein $R_3$ is a linear or branched ($C_1$–$C_5$) alkyl group; or L is $NH_2$, halogen, COOH or $CONR_4R_5$ wherein $R_4$ and $R_5$ are independently hydrogen, or a linear or branched ($C_1$–$C_5$) alkyl which can be substituted by 1–6 hydroxy groups and/or 1–6 alkoxy groups, $R_1$ can have the same meanings as R, independently from it, except for hydrogen, Z is independently OH or $OR_6$, or $NR_4R_5$ wherein $R_4$ and $R_5$ are as previously defined, and $R_6$ is a ($C_1$–$C_{10}$) alkyl, linear or branched, which can be substituted by 1–6 hydroxyl and/or alkoxyl groups, m is between 1 and 5.

9 Claims, No Drawings

BENZYLOXY DERIVATIVES OF DTPA FOR MRI

This invention relates to new compounds which can chelate paramagnetic bi- and trivalent metal ions, their chelates with said metal ions and their use as contrast agents in magnetic resonance imaging (MRI).

From a radiologist's point of view, an improvement in the radiographic image, which means a better contrast enhancement between healthy and diseased tissues, is seen as an aid to the diagnosis which can be obtained through a previous administration of suitable exogen substances.

These substances cause a significant alteration of a specific characteristic, known as relaxivity, of the water protons belonging to the tissue under examination, healthy or diseased, when such water protons are submitted to an external magnetic field. These substances are known as contrast agents for MRI.

In particular this invention relates to new chelating agents of general formula (I) which can be racemic or optically active

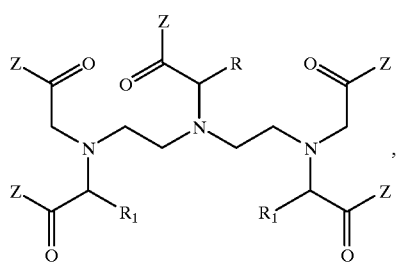

(I)

wherein

R is a —$(CH_2)_m$—O—$R_2$ group or hydrogen, $R_2$ is a ($C_6$–$C_{10}$) aryl, or an alkyl($C_1$–$C_1$)-aryl($C_6$–$C_{10}$) group, substituted or not by a group L corresponding to a OH group or a $OR_3$ group, wherein $R_3$ is a linear or branched ($C_1$–$C_5$) alkyl group; or L is $NH_2$, halogen, COOH or $CONR_4R_5$ wherein $R_4$ and $R_5$ are independently hydrogen, or a linear or branched ($C_1$–$C_5$) alkyl which can be substituted by 1–6 hydroxy groups and/or 1–6 alkoxy groups, $R_1$ can have the same meanings as R, independently from it, except for hydrogen, Z is independently OH or $OR_6$, or $NR_4R_5$ wherein $R_4$ and $R_5$ are as previously defined, and $R_6$ is a ($C_1$–$C_{10}$) alkyl, linear or branched, which can be substituted by 1–6 hydroxyl and/or alkoxyl groups, m is between 1 and 5.

This invention also relates to the chelates of said compounds of formula (I) with bi-trivalent ions of metal elements having an atomic number between 20 and 31, 39, 42, 43, 44, 49, or between 57 and 83, as well as their salts with physiologically compatible organic bases selected from primary, secondary, tertiary amines or basic amino acids, or with inorganic bases whose cations are sodium, potassium, magnesium, calcium or mixtures thereof.

Particularly preferred are the following compounds of formula (II), in which L is as previously defined:

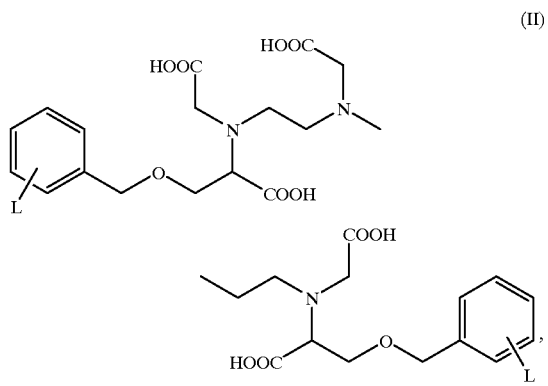

(II)

Equally preferred are the following compounds of formula (III), wherein L is as previously defined:

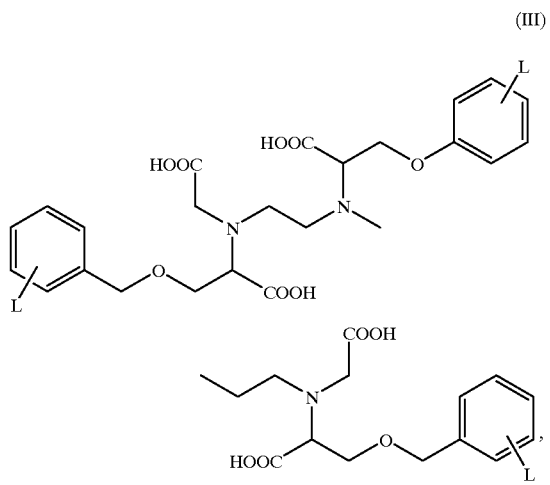

(III)

Preferred chelates are the compounds in which the bi-trivalent metal ion is selected from $Fe^{(2+)}$, $Fe^{(3+)}$, $Gd^{(3+)}$, $Eu^{(3+)}$, $Dy^{(3+)}$, $La^{(3+)}$, $Yb^{(3+)}$ and $Mn^{(2+)}$. Particularly preferred are the chelates of $Gd^{(3+)}$.

Preferred physiologically compatible salifying organic base is selected from ethanolamine, diethanolamine, morpholine, glucamine, N,N-dimethylglucamine, N-methylglucamine, lysine, arginine, ornitine.

Particularly preferred are the following compounds:
(R*,S*)-4-carboxy-5,8,11-tris(carboxymethyl)-1-phenyl-12-[(phenylmethoxy)methyl]-2-oxa-5,8,11-triazatridecan-13-oic acid;
[4S-(4R*,12R*)]-4-carboxy-5,8,11-tris(carboxymethyl)-1-phenyl-12-[(phenylmethoxy)methyl]-2-oxa-5,8,11-triazatridecan-13-oic acid;
[4S-[4R*,8(R*),12R*]]-4-carboxy-5,11-bis(carboxymethyl)-8-[1-carboxy-2-(phenylmethoxy)ethyl]-1-phenyl-12-[(phenylmethoxy)methyl]-2-oxa-5,8,11-triazatridecan-13-oic acid.

The compounds of formula (I) are only included in the general formulas of patent EP 230893, but they are not disclosed or part of the experimental section.

In the cited patent the specific preparation has been generally described, that's to say a process comprising the alkylation of central nitrogen of diethylenetriamine with a b-benzyloxypropionic acid derivative containing a leaving group at the a position.

The repetition of the method of said patent has never led to the obtention of the compounds of formula (I) with acceptable yields from an industrial point of view.

In addition, the above patent does not teach how to carry out a synthesis for optical isomers, when present. On the contrary this synthesis can be easily performed by starting from chiral substrates, in particular from natural amino acids derivatives, thanks to the process of this invention.

A high value of relaxivity in serum can be attributed to a strong bond with plasma proteins which can grant a long permanence in blood. This will allow the use of the products of this invention in order to prepare blood-pool contrast agents for instance in angiographyc diagnostic procedures. And this need led to the preparation of a process for the compounds of formula (I) in view of an industrial exploitation.

This invention also relates to a process for the preparation of complexes of general formula (I), comprising the steps of Scheme 1:

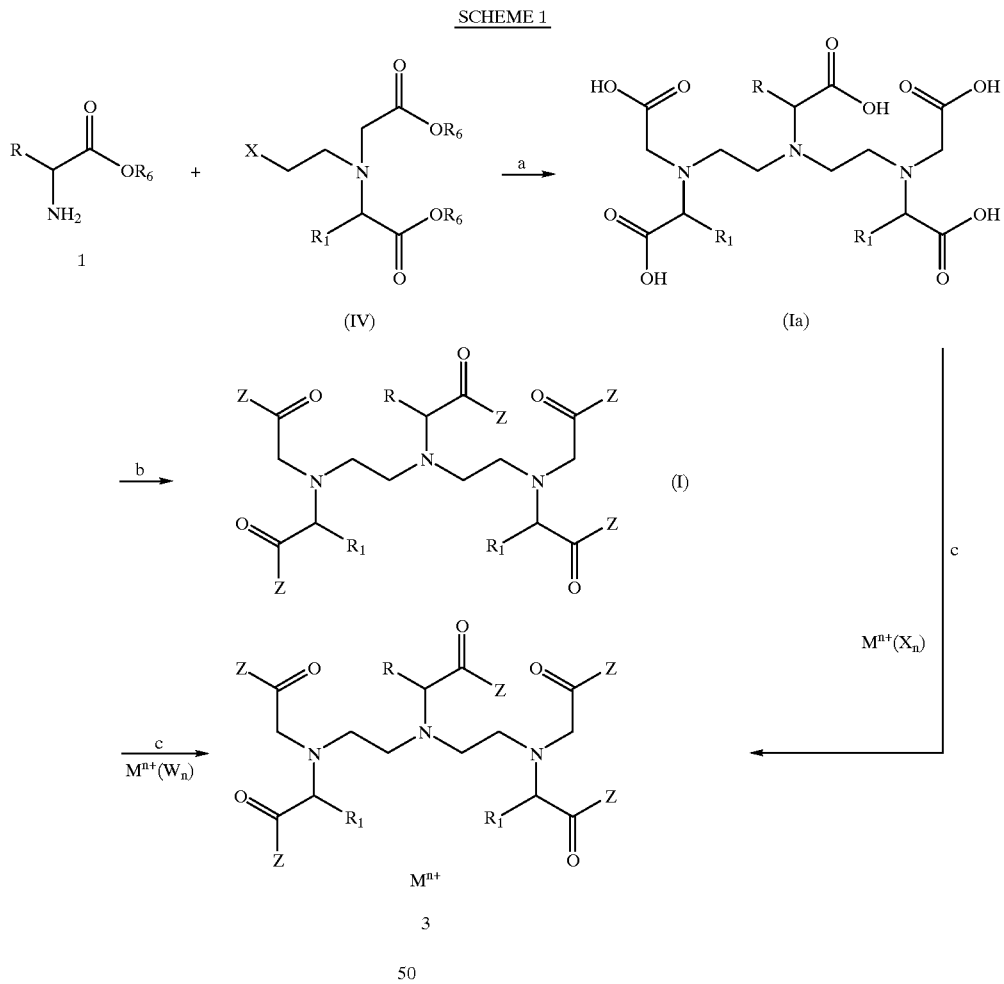

The products of formula (I), specially those containing more aromatic residues, have shown a high relaxivity in human serum, reconstituted by Seronorm®, lyophilized human serum.

Relaxivity is known to be responsible for the contrast enhancement, therefore higher relaxivity values produce a better image contrast, hence relaxivity is used to assess the quality of this type of compounds.

Relaxivity in human serum has two advantages: first, it can mime the district in which the contrast agent will be administered (the biological liquid), differently from the value measured in vitro in saline solution, and, then is highly reproducible thanks to in vitro procedures, in contrast with the in vivo procedures.

The compounds of formula (I) have surprisingly shown very high values of relaxivity, both r1 and r2, in human serum reconstituted from Seronorm®.

wherein R, $R_1$, and $R_6$, are as previously defined and comprising the following steps:

a) reaction of the amino acid precursor of formula 1, racemic or optically active, derivatized as ester to the acid group, with the intermediate of formula (IV), wherein X is a nucleofugal group; reagents 1 and (IV) being used in a molar ratio ranging from 1:2 to 1:4, in a biphase mixture consisting of an aqueous solution buffered at pH 7–11 and an organic solvent and at a temperature of 20–80° C. to give the compounds of formula (Ia), i.e. of formula (I) in which Z is OH;

b) optional transformation of the compounds of formula (Ia) through known reactions into the corresponding ester or amide derivatives, i.e. the compounds of formula (I) in which Z is $OR_6$, or $NR_4R_5$, where $R_4$ $R_5$ and $R_6$ are as defined previously; or direct treatment of the compounds of formula (Ia) according to step c);

c) formation of the desired complex with the ions of metal elements having atomic number ranging from 20 to 31, 39, from 42 to 44, 49 and from 57 to 83 and their salts with physiologically compatible organic bases selected from primary, secondary, tertiary amines or basic amino acids or with inorganic bases whose cations are sodium, potassium, magnesium, calcium, or mixtures thereof, by chelation of the metal ion, preferably carried out by reacting the chelating agents of formula (II) with a metal, in its salt or oxide form ($M^{n+}(W_n)$, $M^{n+}(X_n)$), optionally in the presence of the amount of base or acid necessary to the neutralization to give the relative metal complexes.

In step a) the nucleofugal group is preferably selected from the group consisting of halogen (Cl, Br, I), and reactive residues of sulfonic acid (for instance —OMs, —OTf, —OTs, etc.), and the organic solvent is selected from the group consisting of dimethylsulfoxide, dimethylformamide, dimethylacetamide, hexamethylphosforamide, acetonitrile, N,N'-dimethylpropyleneurea and N-methylpyrrolidone.

Particularly preferred are the following conditions in which step a) of the process of this invention can be performed:

reagent excess equal to 2.1;

organic solvent acetonitrile;

pH ranging from 7 to 9;

temperature ranging from 20 to 40° C.

In addition, this invention relates to new compounds of formula (IV), intermediates in the process for the preparation of compounds of formula (I), according to Scheme 1

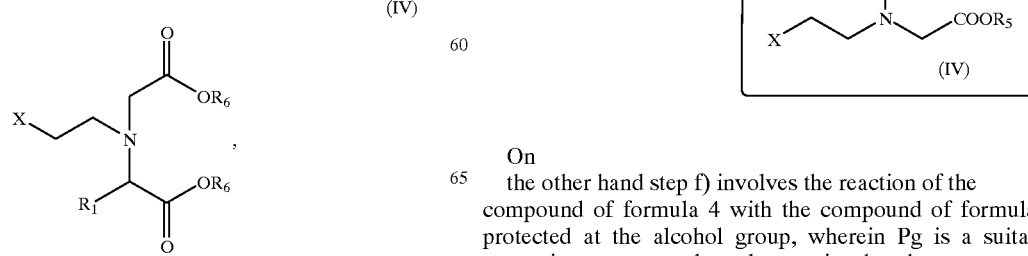

wherein X, $R_1$, and $R_6$ are as previously defined.

This invention also relates to the preparation of compounds of formula (IV), which can be synthesized through two synthetic ways as described in Scheme 2.

SCHEME 2

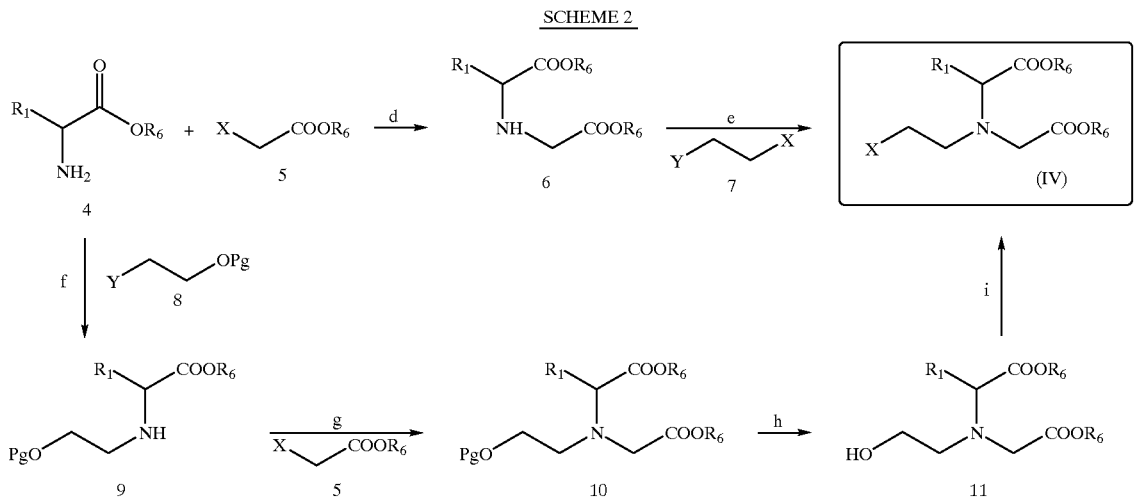

One way foresees steps d) and e) while the other foresees steps f), g), h) and i).

Step d) involves the condensation between the amino acid derivatives of formula 4 and 5, racemic or optically active, esterified to the acid group, under the conditions already described for reaction a) of Scheme 1. Step e) foresees the reaction of compound 6 with an alkylating agent of formula 7, in which X is as previously defined and Y can be the same or another nucleofugal group, to give the intermediate of formula (IV). Alternatively the compound 6 can be reacted with ethylene oxide to give the corresponding hydroxyethyl derivative which is treated, with traditional methods, in order to convert the hydroxyl group in a leaving group according to Scheme 3.

SCHEME 3

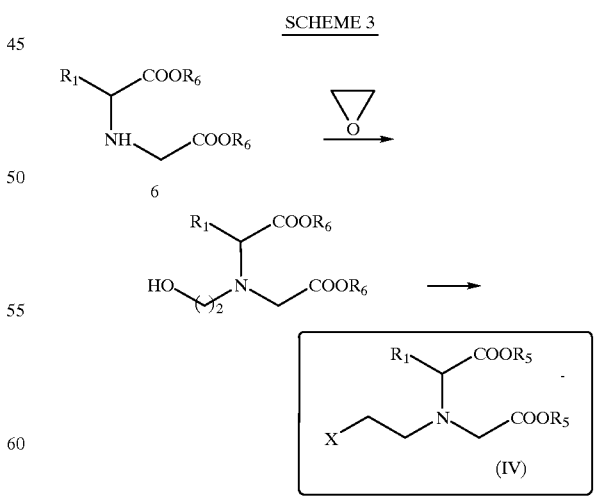

On the other hand step f) involves the reaction of the compound of formula 4 with the compound of formula 8 protected at the alcohol group, wherein Pg is a suitable protecting group, and made reactive by the presence of group X. Afterwards, a condensation reaction with compound 5 is carried out, under the same conditions as in step d), to give the compound 10. Step h) foresees the deprotection of hydroxy group and its successive transformation, according to step i) into the selected nucleofugal X group.

To show the innovative value of the process of this invention, we take as comparative example, the preparation of gadolinium complex of (R*,S*)-4-carboxy-5,8,11-tris(carboxymethyl)-1-phenyl-12-[(phenylmethoxy)-methyl]-2-oxa-5,8,11-triazatridecan-13-oic acid saliffed with 1-deoxy-1-(methylamino)-D-glucitol (1:2) according to the synthetic method of patent EP 230893 (EXAMPLE 2) and the method of this invention (EXAMPLE 4) in the optically active form.

In order to better show the worth of this process, we describe, in Example 1, the synthesis of gadolinium complex of N,N-bis[2-[bis(carboxymethyl)amino]ethyl]-O-phenylmethyl-L-serine salified with 1-deoxy-1-(methylamino)-D-glucitol (1:2), compound, which in its racemic form, has already been claimed in patent EP 230893.

The good water-solubility of the complexed compounds of this invention and the limited osmolality of the solutions are another remarkable quality which make them particularly useful as diagnostic agents.

The compounds of this invention have multiple applications, since they can be administered intravasally (for instance intravenous, intraarterial, intracoronary, intraventricular administrations and so on), intratecally, intraperitoneally, intralymphatically, intracavitally and intraparenquimally. Both soluble and less soluble compounds are useful for the oral and enteral administrations and, therefore, for the imaging of the GI tract.

As far the parenteral administration is concerned, the compounds are preferably formulated as a sterile aqueous solution or suspension, whose pH can range for instance from 6.0 to 8.5.

These aqueous solutions or suspensions can be administered in concentrations ranging from 0.002 to 1.0 mol.

These formulations can be lyophilized and supplied as they are for reconstitution before use.

For the GI use or for the injection in the body cavities, such agents can be formulated as a solution or suspension containing suitable additives which can control viscosity.

In the oral administration they can be formulated according to preparation methods commonly used in the pharmaceutical practice as buffered formulations in order to get additional protection from the stomach acid pH, by preventing the release of the chelated metal ion occurring in particular at pH which are typical of gastric juices.

Other excipients, for instance sweeteners and/or flavouring agents, can also be added according to known techniques of pharmaceutical formulation.

The solutions or suspensions of the compounds of this invention can be formulated as aerosol to be used in aerosol-bronchography and instillation.

In the diagnostic field, the chelates of this invention can be used as radiopharmaceuticals in nuclear medicine, both in the diagnostic and therapeutic sector.

In this case, however, the metal ion which is chelated is a radioisotope, for instance $^{51}$Cr, $^{67}$Ga, $^{68}$Ga, $^{111}$In, $^{99m}$Tc, $^{140}$La, $^{175}$Yb, $^{153}$Sm, $^{166}$Ho, $^{90}$Y, $^{149}$Pm, $^{177}$Lu, $^{47}$Sc, $^{142}$Pr, $^{159}$Gd.

Preferred cations of inorganic bases which can salify the complexes chelates of this invention comprise in particular alkali or alkaline-earth metal ions such as potassium, sodium, calcium, magnesium, and their mixtures.

Preferred cations of organic bases suitable for the above aim, comprise primary, secondary and tertiary amines such as, ethanolamine, diethanolamine, morpholine, glucamine, N-methylglucamine, N,N-dimethylglucamine.

Preferred cations of amino acids comprise, for instance, those of lysine, arginine or ornithine.

The compounds of this invention can also be conjugated to macromolecules or biomolecules or incapsulated or associated with suitable carriers. For instance they can be incapsulated in liposomes or constituents of their chemical structure and used as uni- or bilamellar vesicles.

A list of the preferred compounds of the present invention (described in the Experimental Section) is the following, illustrative of the broad applicability of the invention.

EXAMPLE 1

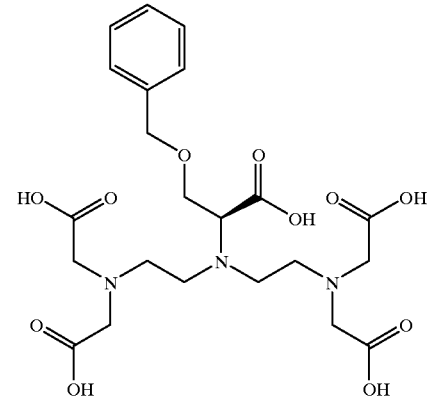

EXAMPLE 2

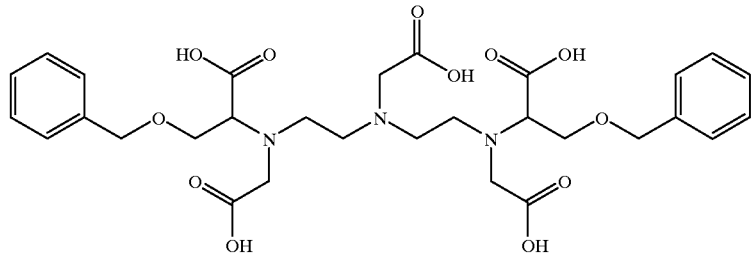

EXAMPLE 3

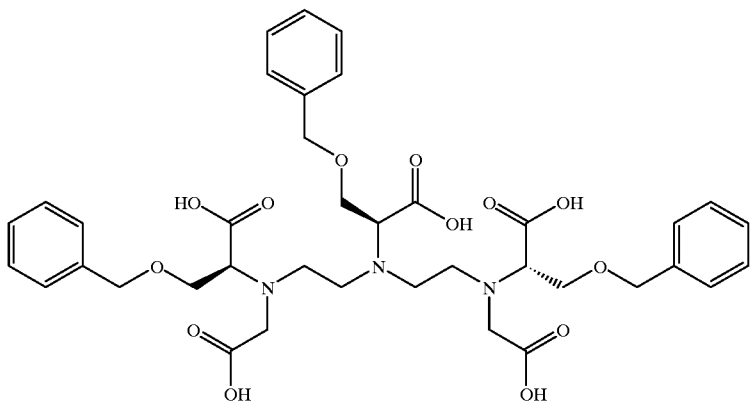

EXAMPLE 4

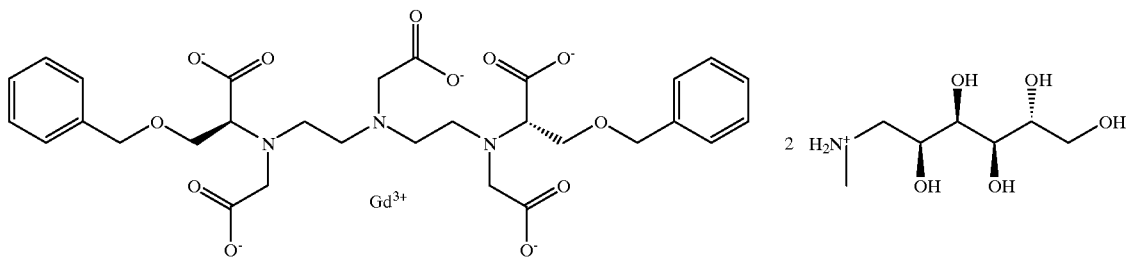

EXPERIMENTAL SECTION

EXAMPLE 1

Gadolinium complex of N,N-bis[2-[bis(carboxymethyl)aminoethyl]-O-phenylmethyl-L-serine salified with 1-deoxy-1-(methylamino)-D-glucitol (1:2).

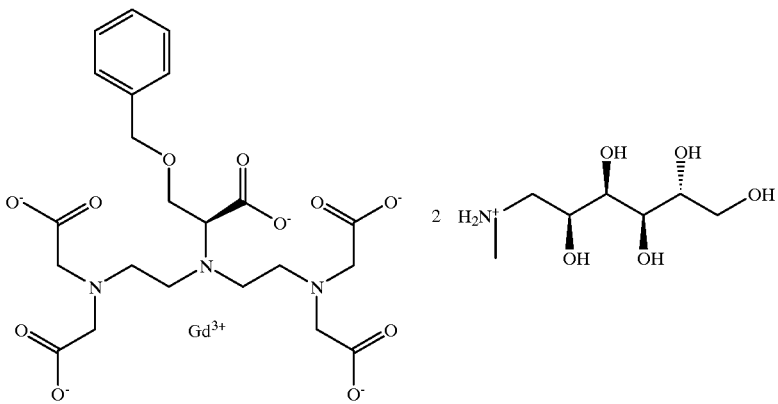

A) O-(phenylmethyl)-L-serine 1,1-dimethylethyl ester.

25 mL of a 70% (w/w) perchloric acid solution (0.29 mol) are added to a suspension containing 25 g of O-(phenylmethyl)-L-serine (marketed product) (0.13 mol) in 448.2 g of t-butyl acetate(3.86 mol) and 39.3 g of t-BuOH (0.53 mol) at 40° C. Then, the solution is cooled to room temperature and kept under stirring and under inert atmosphere for a prolonged period. The reaction mixture is washed repeatedly with H₂O, 5% Na₂CO₃ (w/w) and H₂O. The organic phase is dried and concentrated; then the residue is purified through chromatography, to give 16.4 g of the desired product (65 mmol).

Yield: 50%; K.F.: 0.41% (w/w); GC: 100% (% in area);

| Elemental analysis | C | H | N | H₂O |
|---|---|---|---|---|
| % calc.: | 66.91 | 8.42 | 5.57 | |
| % found: | 67.57 | 8.61 | 5.26 | |
| % corresp. to: | 67.85 | 8.60 | 5.28 | on anhydrous |

TLC: Silica gel plate 60F 254 Merck; Eluent: CHCl₃:CH₃COCH₃=8:2 (v/v); Detector: 0.5% KMnO₄ (w/w) in 1N NaOH Rf=0.4; ¹H-NMR, ¹³C-NMR, IR and MS spectra are consistent with the structure.

B) N-(2-bromoethyl)-N-[2-(1,1-dimethylethoxy)-2-oxoethyl]glycine 1,1-dimethylethyl ester.

15.15 g of ethanolamine (marketed product) (0.25 mol) are dropwise added to a suspension containing 112.3 g of t-butyl bromoacetate (marketed product) (0.58 mol) and 62.57 g of KHCO₃ (0.62 mol) in 400 mL of DMF, kept at 0° C. and under inert atmosphere. The temperature is raised to 20° C. and, after 22 h, the suspension is dissolved with a saturated solution of NaHCO₃ and Et₂O. After the separation of the phases, the aqueous phase is extracted with Et₂O repeatedly and the collected organic phases are dried over Na₂SO₄ and concentrated. 100 g of a yellow oil are obtained that are dissolved in 700 mL of CH₂Cl₂. 79.76 g of triphenylphosphine (marketed product) (0.30 mol) are added and, after cooling to 0° C., 53.4 g of solid N-bromosuccinimide (marketed product) (0.30 mol) are added. After 2.5 h the reaction is completed and the solution is concentrated to dryness and dissolved in 500 mL of Et₂O. The precipitated salts are filtered off. The solution is diluted with additional 500 mL of Et₂O. After 16 h at 4° C. the precipitated salts are filtered and the solution is concentrated and purified through flash chromatography. After concentration to dryness 57 g of the desired product (0.16 mol) are obtained.

Yield: 65%; K.F.: 0.1% (w/w); GC: 99% (% in area);

| Elemental analysis | C | H | N | Br |
|---|---|---|---|---|
| % calc.: | 47.73 | 7.44 | 3.98 | 22.68 |
| % found: | 47.86 | 7.50 | 4.03 | 22.49 |

TLC: Silica gel plate 60F 254 Merck; Eluent: n-hexane : EtOAc=9:1 (v/v)B; Detector: 0.5% KMnO₄ (w/w) in 1N NaOH Rf=0.4; ¹H-NMR, ¹³C-NMR, IR and MS spectra are consistent with the structure.

C) N,N-bis[2-[bis[2-(1,1-dimethylethoxy)-2-oxoethyl]-amino]ethyl]-O-phenylmethyl-L-serine 1,1-dimethylethyl ester.

200 mL of a phosphate buffer 2M at pH 8 are added to a solution containing 50.37 g of compound B) (0.143 mol) and 16.4 g of compound 1A) (0.065 mol) in 400 mL di CH₃CN. The reaction mixture is kept under stirring for 2 h, the phases are separated and 200 mL of a 2M phosphate buffer are added to the organic phase and the whole is kept under stirring for 18 h. The organic phase is washed with a NaCl saturated solution, dried over Na₂SO₄ and concentrated to dryness. The resulting oil (70 g) is purified through flash chromatography and concentrated to dryness to give 38 g of the desired product (0.048 mol).

Yield: 74%; K.F.: 0.1% (w/w); HPLC: 99% (% in area);

| Elemental analysis | C | H | N |
|---|---|---|---|
| % calc.: | 63.53 | 9.01 | 5.29 |
| % found: | 64.01 | 9.30 | 5.26 |

TLC: Silica gel plate 60F 254 Merck; Eluent: n-hexane : EtOAc=8:2 (v/v); Detector: 0.5% KMnO₄ (w/w) in 1N NaOH Rf=0.4; ¹H-NMR, ¹³C-NMR, IR and MS spectra are consistent with the structure.

D) N,N-Bis[2-[bis(carboxymethyl)amino]ethyl]-O-phenylmethyl-L-serine.

5.87 g of iodotrimethylsilane (marketed product) (29.3 mmol) are added to a solution containing 2.33 g of compound 1C) (2.93 mmol) in 50 mL of CHCl₃ kept under stirring under inert atmosphere at 10° C. After 20 h at 25° C. 30 mL of H₂O are added. After 15 min the phases are separated and the aqueous phase, after being washed some times with Et₂O, is concentrated to a volume of 10 mL and adjusted to pH 1.7 with 4N NaOH. The solution is loaded on a column Amberlite® XAD 1600 eluting with H₂O up to the removal of iodides, then with a H₂O/CH₃OH gradient. The fractions containing the product are evaporated to dryness to give 1.1 g of the desired product (2.14 mmol).

Yield: 73% m.p.: 96–98° C.; K.F.: 0.73%(w/w); HPLC: 100% (% in area);

| Elemental analysis | C | H | N | H₂O |
|---|---|---|---|---|
| % calc.: | 51.46 | 6.08 | 8.18 | |
| % found: | 50.71 | 6.11 | 8.05 | |
| % corresp. to | 51.08 | 6.03 | 8.11 | on anhydrous |

¹H-NMR, ¹³C-NMR, IR and MS spectra are consistent with the structure.

E) Gadolinium complex of N,N-bis[2-[bis(carboxyme-thyl)amino]ethyl]-O-phenylmethyl-L-serine salified with 1-deoxy-1-(methylamino)-D-glucitol (1:2).

1.84 g of Gd₂O₃ (marketed product) (5.06 mmol) are added to a solution containing 5.2 g del compound D) (10.13 mmol) and 3.95 g of 1-deoxy-1-(methylamino)-D-glucitol (marketed product) (20.26 mmol) in 100 mL of H₂O. The suspension is kept under stirring at 60° C. for 3 h. After cooling, the solution is filtered on a filter Millipore(R) (HA 0.45 μm) and evaporated to dryness to give 10.70 g of the desired product (10.11 mmol).

Yield: quantitative m.p.: >200° C. dec.;

K.F.: 1.40% (w/w); HPLC: 100% (% in area);

| Elemental analysis | C | H | N | Gd | H$_2$O |
|---|---|---|---|---|---|
| % calc.: | 40.86 | 5.91 | 6.62 | 14.86 | |
| % trov.: | 40.89 | 6.49 | 6.28 | 13.70 | |
| % corresp. to: | 41.40 | 6.03 | 6.70 | 14.56 | on anhydrous |

TLC: Silica gel plate 60F 254 Merck; Eluent: n-propanol:NH$_4$OH 25% (w/w)=9:1 (v/v); Detector: KMnO$_4$ 0.5% (w/w) in 1N NaOH Rf=0.35;

EXAMPLE 2

Gadolinium complex of (R*,S*)-4-carboxy-5,8,11-tris (car-boxymethyl)-1-phenyl-12-[(phenylmethoxy)methyl3-2-oxa-5,8,11-triazatridecan-13-oic acid salified with 1-deoxy-1-(methylamino)-D-glucitol (1:2).

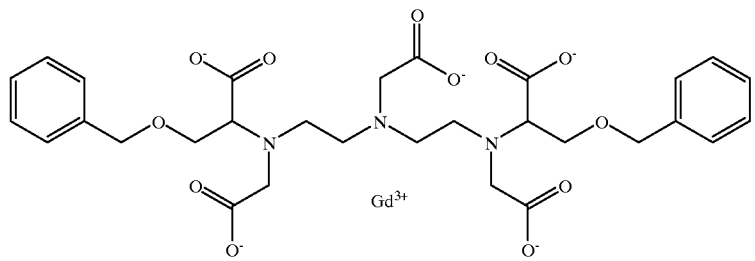
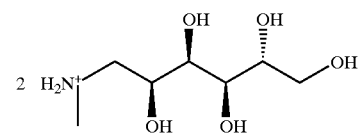

A) (R*,S*)-4-carboxy-5,8,11-tris(carboxymethyl)-1-phenyl-12-[(phenylmethoxy)methyl]-2-oxa-5,8,11-triazatridecan-13-oic acid.

97.2 g of solid 2-chloro-3-phenylmethoxypropionic acid (0.45 mol) [prepared according to the procedure of Grassman, W.; Wünsch, AND.; Deufel, P.; Zwick, A. *Chem. Ber.* 1958, 91, 538, for the analogous bromo-derivative] are added under stirring to a solution containing 23.36 g of diethylenetriamine (1 mol) (marketed product) in 60 mL of H$_2$O, cooled to 0° C. and kept at pH 10 through addition of NaOH 6M,. When the addition is completed the whole is heated to 50° C. and kept reacting for 4 h then is cooled to room temperature. The reaction crude (60.42 g) is purified on ion exchange resin (strong anionic) and then on a polystyrene resin.

A solution containing 82.76 g of bromoacetic acid (0.596 mol) in 125 mL of H$_2$O and a NaOH 6N solution are added to a solution containing 60.42 g of the purified product sodium salt (1:2) (0.12 mol) in 300 mL of H$_2$O kept at 70° C., at pH 10 and under vigorous stirring. When the addition is completed, the whole is stirred for 1 h keeping pH 10 through addition of 125 mL of 6N NaOH. After that, a solution of 16.59 g of bromoacetic acid (0.12 mol) in 50 mL of H$_2$O is added, reacting at about pH 10 with 50 mL of 6N NaOH, for 1.5 h. The solution is cooled, the pH is adjusted to 7 with 12N HCl. The crude is purified, the ph of the solution is adjusted to 2 with H$_3$PO$_4$, and the product is salted-off. After evaporation and drying, 18.20 g of the desired product (0.029 mol) are obtained.

Yield: 24% m.p.: 82–84° C.; K.F.: 2.32% (w/w); HPLC: 96% (% in area);

| Elemental analysis | C | H | N | Na$^+$ | Cl$^-$ | H$_2$O |
|---|---|---|---|---|---|---|
| % calc.: | 56.87 | 6.20 | 6.63 | absent | absent | |
| % found: | 54.84 | 6.24 | 6.20 | <0.1 | <0.1 | |
| % corresp. to: | 56.14 | 6.10 | 6.35 | | | on anhydrous |

$^1$H-NMR, $^{13}$C-NMR, IR and MS spectra are consistent with the structure.

B) Gadolinium complex of (R*,S*)-4-carboxy-5,8,11-tris (carboxymethyl)-1-phenyl-12-[(phenylmethoxy)methyl]-2-oxa-5,8,11-triazatridecan-13-oic acid salified with 1-deoxy-1-(methylamino)-D-glucitol (1:2).

3.91 g of Gd$_2$O$_3$ (10.78 mmol) are added to a solution containing 14.01 g of compound A) (21.56 mmol, dry) and 8.42 g of 1-deoxy-1-(methylamino)-D-glucitol (43.12 mmol) in 150 mL of H$_2$O. The suspension is kept under stirring at 50° C. for 4 h. After filtration on Millipore(R) (HA 0.45 mm), the solution is added with Carbopuron 4N and kept under stirring for 1.5 h. The solution is filtered on paper and then on Millipore® (HA 0.45 mm) and the solvent is evaporated off to obtain 23.56 g of the desired product (19.99 mmol).

Yield: 93% m.p.: 103–104° C.; K.F.: 6.64% (w/w); HPLC: 95% (% in area);

| Elemental analysis | C | H | N | Gd | H$_2$O |
|---|---|---|---|---|---|
| % calc.: | 44.85 | 5.99 | 5.94 | 13.35 | |
| % found: | 42.49 | 6.32 | 5.40 | 12.14 | |
| % corresp. to: | 45.51 | 5.98 | 5.78 | 13.00 | on anhydrous |

EXAMPLE 3

Gadolinium complex of [4S-[4R*,8(R*),12R*]]-4-carboxy-5,11-bis(carboxymethyl)-8-[1-carboxy-2-(phenylmethoxy)ethyl]-1-phenyl-12-[(phenylmethoxy)methyl]-2-oxa-5,8,11-triazatridecan-13-oic acid salified with 1-deoxy-1-(methylamino)-D-glucitol (1:2)

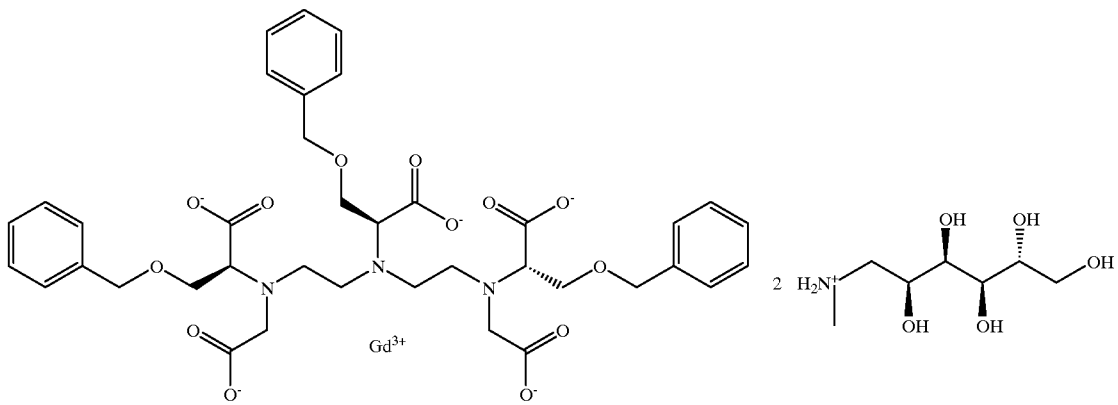

A) N-[2-(1,1-dimethylethoxy)-2-oxoethyl]-O-(phenylmethyl)-L-serine 1,1-dimethylethyl ester.

500 mL of a 2M phosphate buffer at pH 8 are added to a solution containing 60 g of compound A) of EXAMPLE 1 (0.24 mol) and 53.6 g of t-butyl bromoacetate (marketed product) (0.275 mol) in 500 mL of $CH_3CN$. The biphase mixture is kept under stirring for 18 h at 20° C. After separation, the organic phase is reduced to oil and dissolved in 500 mL of a mixture $CHCl_3/H_2O=1/1$ (v/v).

The organic phase is dried over $Na_2SO_4$ and concentrated to give 82 g of an oily residue, which is purified through flash chromatography to give 67 g of the desired product (0.18 mol).

Yield: 76%; HPLC: 100% (% in area); TLC: Silica gel plate 60F 254 Merck; Eluent: n-hexane : EtOAc=9:1 (v/v); Detector: o.5% $KMnO_4$ (w/w) in iN NaOH Rf=0.4; $^1$H-NMR, $^{13}$C-NMR, IR and MS spectra are consistent with the structure.

B) N-(2-bromoethyl)-N-[2-(1,1-dimethylethoxy)-2-oxoethyl ]-O-(phenylmethyl)-L-serine 1,1-dimethylethyl ester.

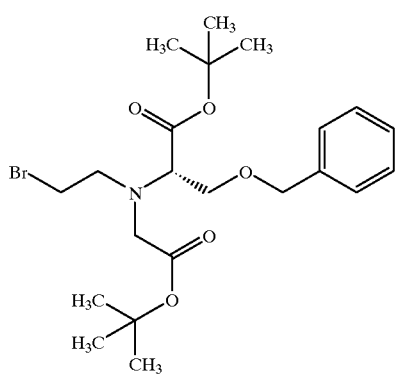

A solution containing 66 g of compound A) (0.18 mol) in 1526 g of 1,2-dibromoethane and 116.3 g of N,N-diisopropylethylamine (0.90 mol) is kept at 80° C. and under inert atmosphere for 50 h. After cooling to 0–5° C., the precipitated salts are filtered off and the solution is washed repeatedly with $H_2O$, dried over $Na_2SO_4$, and concentrated. The resulting 100 g of oil are purified through flash chromatography. After concentration to dryness, 34 g of the desired product (0.072 mol) are obtained.

Yield: 40%; HPLC: 96% (% in area); TLC: Silica gel plate 60F 254 Merck; Eluent: n-hexane : EtOAc=9:1 (v/v); Detector: 0.5% $KMnO_4$ (w/w) in 1N NaOH Rf=0.6; $^1$H-NMR, $^{13}$C-NMR, IR and MS spectra are consistent with the structure.

C) [4S-[4R*,8(R*),12R*]]-4-[(1,1-dimethylethoxy) carbonyl ]-5,11-bis[2-(1,1-dimethylethoxy)-2-oxoethyl]-8-[1-[(1,1-dimethylethoxy)carbonyl]-2-(phenylmethoxy) ethyl]-1-phenyl-12-[(phenylmethoxy)methyl]-2-oxa-5,8,11-triazatridecan-13-oic acid 1,1-dimethylethyl ester. 500 mL of 2M phosphate buffer at pH 8 are added to a solution containing 9.0 g of compound A) of EXAMPLE 1 (0.036 mol) and 34 g of compound B) (0.072 mol) in 500 mL of $CH_3CN$. The biphase solution is kept under stirring for 20 h. After separation, the organic phase is separated, concentrated to oil and dissolved in 500 mL of a $CH_2Cl_2/H_2O =1/1$ (v/v) mixture. After separation, the organic phase is dried over $Na_2SO_4$ and concentrated. The resulting 48 g of oil are purified through flash chromatography. After concentration to dryness, 30 g of the desired product (0.029 mol) are obtained.

Yield: 80%; HPLC: 99% (% in area); TLC: Silica gel plate 60F 254 Merck; Eluent: n-hexane : EtOAc=9:1 (v/v); Detector: 0.5% $KMnO_4$ (w/w) in 1N NaOH Rf=0.3; $^1$H-NMR, $^{13}$C-NMR, IR and MS spectra are consistent with the structure.

D) [4S-[4R*,8(R*),12R*]]-4-carboxy-5,11-bis (carboxymethyl)-8-[1-carboxy-2-(phenylmethoxy)ethyl]-1-phenyl-12-[(phenylmethoxy)methyl]-2-oxa-5,8,11-triazatridecan-13-oic acid. 52.75 g of iodotrimethylsilane (marketed product) (0.26 mol) are dropwise added to a solution containing 27.26 g of compound C) (26.35 mmol) in 150 mL of $CHCl_3$, kept at 5–10° C. and under inert atmosphere during 30 min. The solution is kept under stirring at 20° C. for 20 h. 100 mL of $H_2O$ are added to give a red viscous precipitate which is dissolved in 250 mL of $CH_3CN$. The solution is concentrated to dryness. The resulting solid is dissolved in 150 mL of $H_2O$ and added with NaOH 2N up to pH 10, i.e. to complete solubilization. The solution is adjusted to pH 1.8 with 6N HCl, giving a white precipitate which is filtered and washed with $H_2O$ up to remove completely chlorides, thereby giving 15.1 g of a solid. Then the solid is diluted with 50 mL of 2propanol, dissolved to ebullition, cooled to 20° C. and filtered to give 14.8 g of the desired product (19.6 mmol).

Yield: 74% m.p.: 96–98° C.; K.F.: 1.42% (w/w); HPLC: 94% (% in area);

| Elemental analysis | C | H | N | H$_2$O |
|---|---|---|---|---|
| % calc.: | 60.55 | 6.28 | 5.57 | |
| % found: | 58.95 | 6.44 | 5.26 | |
| % corresp. to: | 59.80 | 6.37 | 5.33 | on anhydrous |

$^1$H-NMR, $^{13}$C-NMR, IR and MS spectra are consistent with the structure.

E) Gadolinium complex of [4S-[4R*,8(R*),12R*]]-4-carboxy-5,11-bis(carboxymethyl)-8-[1-carboxy-2-(phenylmethoxy)ethyl]-1-phenyl-12-[(phenylmethoxy)methyl]-2-oxa-5,8,11-triazatridecan-13-oic acid salified with 1-deoxy-1-(methylamino)-D-glucitol (1:2).

2p2.69 g of Gd$_2$O$_3$ (7.43 mmol) are added to a solution containing 11.2 g of compound D) (14.9 mmol) and 5.80 g of 1-deoxy-1-(methylamino)-D-glucitol (marketed product) (29.7 mmol) in 150 mL of H$_2$O. The suspension is kept at 70° C. for 5 h. The solution is filtered on Millipore® (HA 0.45 μm), concentrated to a small volume (60 mL) and loaded on a column of resin Amberlite® XAD 1600 (600 mL) and then eluted with H$_2$O up to the removal of chlorides and then with a gradient H$_2$O/CH$_3$OH=50/50 (v/v). After concentration to dryness, 17.1 g of the desired product (13.1 mmol) are obtained.

2pYield: 88% m.p.: 205° C. dec.; K.F. : 4.95% (w/w); HPLC: 97% (% in area); Free metal: <0.1%;

| Elemental analysis | C | H | N | Gd | H$_2$O |
|---|---|---|---|---|---|
| % calc.: | 48.10 | 6.05 | 5.39 | 12.11 | |
| % found: | 46.01 | 6.09 | 5.11 | 11.55 | |
| % corresp. to: | 48.41 | 5.83 | 5.38 | 12.15 | on anhydrous |

EXAMPLE 4

2pGadolinium complex of [4S-(4R*,12R*)]-4-carboxy-5,8,11-tris(carboxymethyl)-1-phenyl-12-[(phenylmethoxy)methyl]-2-oxa-5,8,11-triazatridecan-13-oic acid salified with 1-deoxy-1-(methylamino)-D-glucitol (1:2).

2pThe desired complex is prepared according to Example 3 starting from glycine 1,1-dimethylethyl ester (CAS RN 6456-74-2, ) and from 1,1-dimethylethyl ester of N-(2-bromoethyl)-N-[2-(1,1-dimethylethoxy)-2-oxoethyl]-O-(phenylmethyl)-L-serine.

EXAMPLE 5

Relaxivity Measurements (r1 and r2) in Human Serum

2pThe following Table illustrates r1 and r2 values, in saline solution and in human serum, and their comparison with the values of MAGNEVIST® (Gd-DTPA N-methylglucamine salt produced by Schering) and Gd-Bopta/Dimeg.

TABLE

| | r1 (s$^{-1}$mM$^{-1}$) Saline solution | r2 (s$^{-1}$mM$^{-1}$) Saline solution | r1 (s$^{-1}$mM$^{-1}$) HUMAN SERUM | r2 (s$^{-1}$mM$^{-1}$) HUMAN SERUM |
|---|---|---|---|---|
| MAGNEVIST$^{(R)}$ | 3.77 | 4.73 | 4.96 | 5.43 |
| Gd-BOPTA/Dimeg | 4.63 | 5.65 | 9.31 | 11.19 |
| EXAMPLE 2 | 5.24 | 6.08 | 26.45 | 30.70 |
| EXAMPLE 3 | 6.78 | 7.77 | 46.90 | 57.00 |

2pIn this table it can be noted that, for the same compound, the relaxivity in lyophilized human serum has extraordinarily higher values than the corresponding values in saline solution.

What is claimed is:

2p1. A compound of formula (II) or (III) which is in a racemic form or in an optically active form:

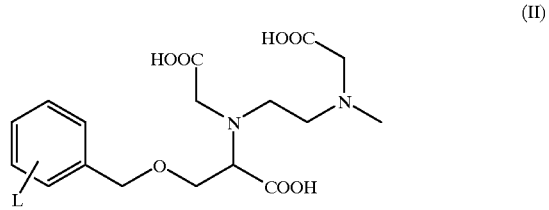
(II)

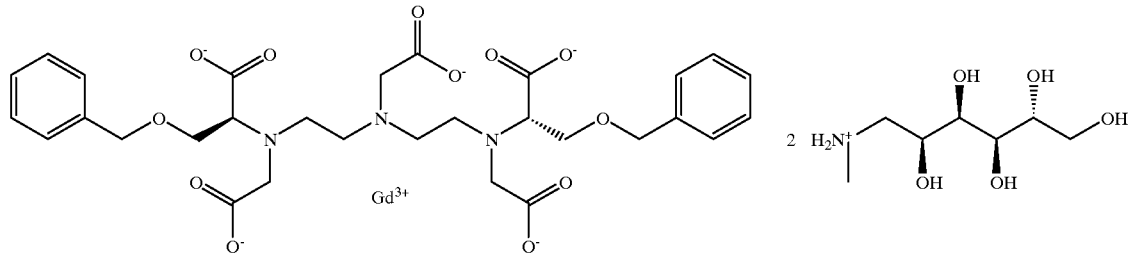

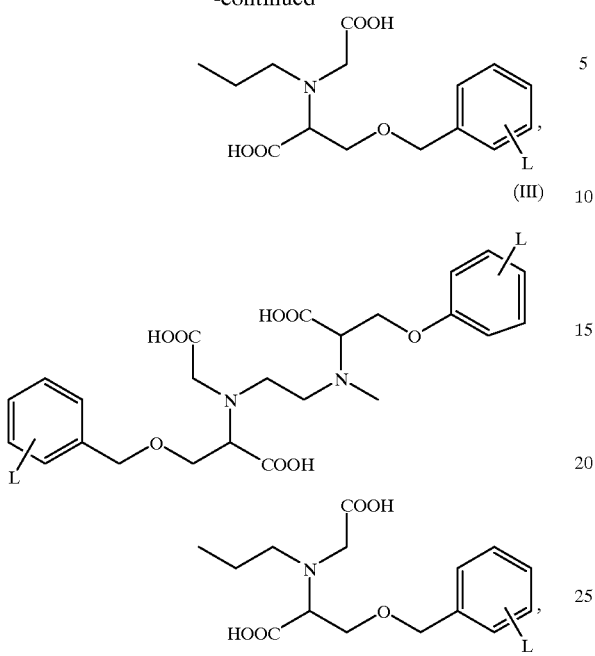

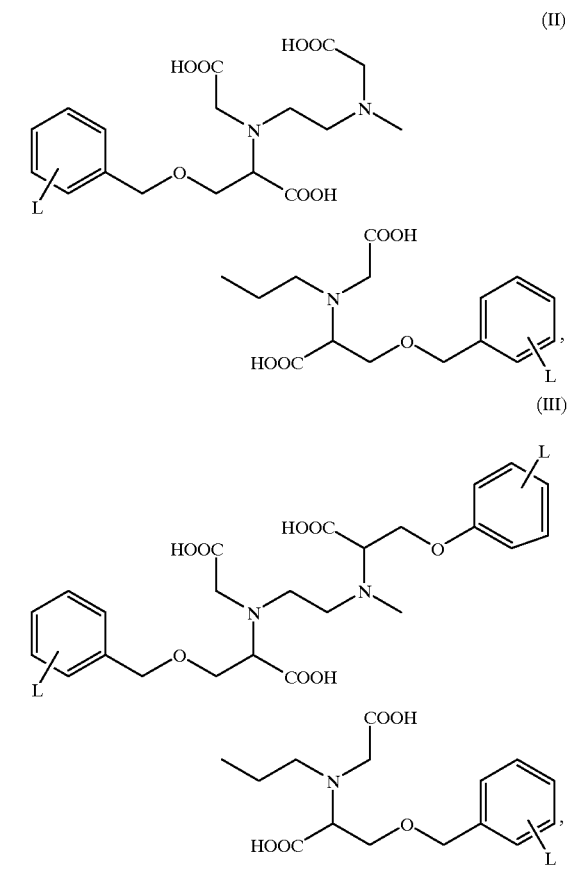

wherein L is an OH group or an $OR_3$ group, where $R_3$ is a linear or branched ($C_1$–$C_5$) alkyl group; or L is $NH_2$, halogen, COOH or $CONR_4R_5$ where $R_4$ and $_5$ are independently hydrogen, or a linear or branched ($C_1$–$C_5$) alkyl which can be substituted by 1–6 hydroxy groups and/or 1–6 alkoxy groups, as well as their chelates with bi-travelent ions of metal elements having an atomic number between 20 and 31, 39, 42, 43, 44, 49, or between 57 and 83, as well as bases selected from primary, secondary, tertiary amines or basic amino acids, or with inorganic bases whose cations are sodium, potassium, magnesium, calcium or mixtures thereof.

2. A compound according to claim 1, wherein the bi- or trivalent metal ion is selected from the group consisting of $Fe^{(2+)}$, $Fe^{(3+)}$, $Gd^{(3+)}$, $Eu^{(3+)}$, $Dy^{(3+)}$, $La(^3$, $Yb^{(3+)}$ and $Mn^{(2+)}$.

3. A compound according to claim 2, in which the metal ion is $Gd^{(3+)}$.

4. A compound according to claim 1, wherein the physiologically compatible organic base is selected from the group consisting of ethanolamine, diethanolamine, morpholine, glucamine, N,N-dimethylglucamine, N-methylglucamine, lysine, arginine and ornithine.

5. A compound selected from the group consisting of:
(R*, S*)-4-carboxy-5,8,11-tris(carboxymethyl)-1-phenyl-12-[(phenylmethoxy) methyl]-2-oxa-5,8,11-triaza-tridecan-13-oic acid
[4S-(4R*, 1 2R*)]-4-carboxy-5,8,11 -tris (carboxymethyl)-1-phenyl-12-[(phenylmethoxy) methyl]-2-oxa-5,8,11 -triazatridecan-13-oic acid; and
[4S-[4R*, 8(R*), 12R* ]]-4-carboxy-5, 11 -bis (carboxymethyl)-8-[1 -carboxy-2-phenylmethoxy) ethyl]- 1-phenyl-12-[(phenylmethoxy)methyl]-2-oxa-5,8,11 -triazatridecan-13-oic acid.

6. A diagnostic contrast composition for imaging of organs and/or tissues of the human or animal body comprising, together with a pharmaceutically acceptable carrier or diluent, a compound of formula (II) or (III) which is in a racemic form or in an optically active form:

wherein L is an OH group or an $OR_3$ group, where $R_3$ is a linear or branched ($C_1$–$C_5$) alkyl group; or L is $NH_2$, halogen, COOH or $CONR_4R_5$ where $R_4$ and $_5$ are independently hydrogen, or a linear or branched ($C_1$–$C_5$) alkyl which c an be substituted by 1–6 hydroxy groups and/or 1–6 alkoxy groups, as well as their chelates with bi-trivalent ions of metal elements having an atomic number between 20 and 31, 39, 42, 43, 44, 49, or between 57 and 83, as well as bases selected from primary, secondary, tertiary amines or basic amino acids, or with inorganic bases whose cations are sodium, potassium, magnesium, calcium or mixtures thereof.

7. A diagnostic composition of claim 6 further including a viscosity agent, a buffer or excipient.

8. A method of magnetic resonance imaging a human or animal comprising administering the diagnostic composition of claim 6 to a human or animal to be imaged and thereafter magnetic resonance imaging.

9. A method of angiographic diagnosing a human or animal comprising administering the diagnostic composition of claim 6 to a human or animal and thereafter angiographically imaging.

* * * * *